Figure 1:
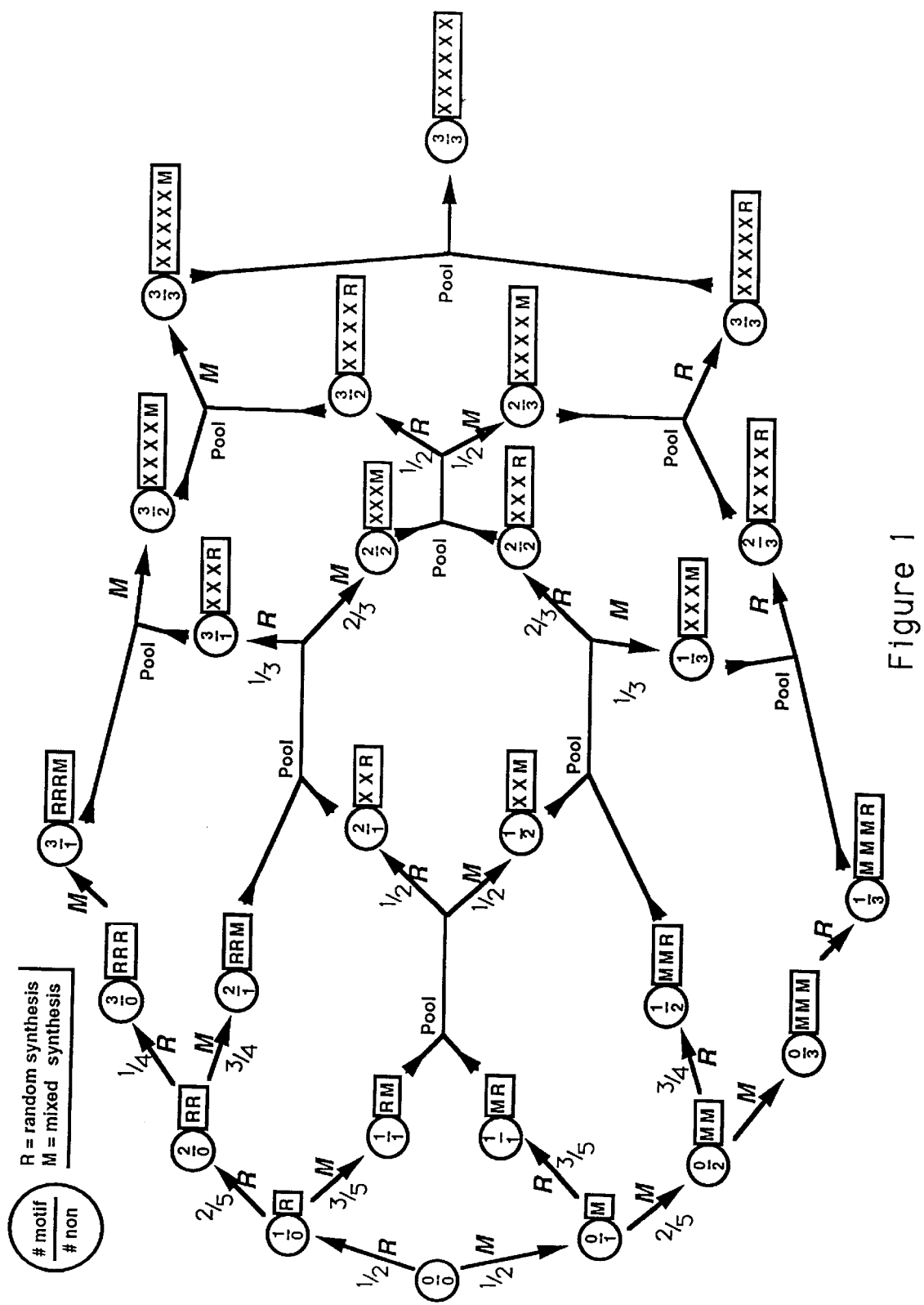

US005846841A

United States Patent [19]
Sepetov et al.

[11] Patent Number: 5,846,841
[45] Date of Patent: Dec. 8, 1998

[54] MOTIF LIBRARIES

[75] Inventors: Nikolai Sepetov; Victor Krchnak; Michal Lebl, all of Oro Valley, Ariz.

[73] Assignee: Selectide Corporation, Tucson, Ariz.

[21] Appl. No.: 754,878

[22] Filed: Nov. 22, 1996

Related U.S. Application Data

[63] Continuation of Ser. No. 246,435, May 20, 1994, abandoned.
[51] Int. Cl.$^6$ .................................................... G01N 33/53
[52] U.S. Cl. ........................... 436/518; 435/7.1; 436/501; 530/333; 530/334
[58] Field of Search .............................. 435/7.1; 436/501, 436/518, 524, 531; 530/333, 334, 300; 536/1.11, 18.5, 18.6, 25.3

[56] References Cited

U.S. PATENT DOCUMENTS

| | | | |
|---|---|---|---|
| 4,631,211 | 12/1986 | Houghten | 428/35.5 |
| 4,833,092 | 5/1989 | Geysen | 436/501 |
| 5,010,175 | 4/1991 | Rutter et al. | 530/334 |
| 5,182,366 | 1/1993 | Huebner et al. | 530/334 |
| 5,194,392 | 3/1993 | Geysen | 436/518 |
| 5,565,325 | 10/1996 | Blake | 435/7.1 |

FOREIGN PATENT DOCUMENTS

| | | |
|---|---|---|
| 86/00991 | 2/1986 | WIPO . |
| WO 92/00091 | 1/1992 | WIPO . |

OTHER PUBLICATIONS

Hirschmann et al., J. Am. Chem. Soc., vol. 114, pp 9699–9701 (1992) "The First Design and Synthesis of a Steroidal Peptidomimetic. The Potential Value of Peptidomimetics in Elucidating the Bioactive Conformation of Peptide Ligands".

Brenner at al., Proc. Natl. Acad. Sci., vol. 89 (1992), pp5381–5383 "Encoded Combinatorial Chemistry".

Furka, et al. 1991, Int. J. Protein Res. 37:487–493.

Houghten et al., 1991, Nature, 354:82–86.

Lam et al., 1991, Nature, 354:82–84.

Lam et al., 1993, Bioorg Med. Chem. Lett. 31:419.

Vagner et al., 1993, "Novel Methodology for Differentiation of " Surface and Interior Areas of Polyoxyethylene–Polystyrene (POE–PS) Supports: Application to Library Screening Procedures in Innovation and Perspectives in Solid Phase Synthesis and Related Technologies ed. by Epton, R.

Chen et al., "Biased Combinatorial Libraries: Novel Ligands for the SH3 Domain of Phosphatidylinositol 3–Kinase", J. Am. Chem. Soc., vol. 115, pp 12591–12592 (1993).

*Primary Examiner*—Lora M. Green
*Attorney, Agent, or Firm*—Pennie & Edmonds LLP

[57] ABSTRACT

The invention concerns libraries of chemical compounds, that are useful in medicinal chemistry and related arts, their methods of manufacture and methods of their use. In one embodiment the individual chemical species of the library are synthesized aleatoricly, i.e, by a process involving chance. The chemical species of the library are used while attached to solid phase supports. The library differs from previously disclosed libraries that were intended to be screened while in solid phase in that each individual solid phase support or identifiable portion of a solid phase array displays many species of ligands, collectively termed a "set." The library is constructed so that each set contains a single invariant structure, common to all the species of ligands attached to the particular solid phase support, which is termed a "motif." The invention teaches that libraries of motifs can be employed advantageously compared to known libraries wherein a single species is present on each support.

27 Claims, 2 Drawing Sheets

MOTIF LIBRARIES

This is a continuation of application Ser. No. 08/246,435, filed May 20, 1994 now abandoned.

1. FIELD OF THE INVENTION

The present invention concerns manufactures, methods of their synthesis and methods of their use, that are useful to discover ligands for known acceptor molecules of interest. Typical acceptors are enzymes, such as blood clotting or complement factors, cell surface proteins such as neurotransmitter, hormone and growth factor receptors, and cell surface transport molecules. Ligands can be either antagonists or agonists or can be functionally neutral and useful to identify or label the acceptor. Conventionally medicinal chemists search for such ligands by is synthesizing individual candidate molecules of predetermined structure and testing each for activity. Recent inventions have produced great efficiencies through the simultaneous synthesis of large collections, termed libraries, of many millions of aleatoricly synthesized polymers, typically peptides, which are then "screened" by exposure to the acceptor of interest to detect rare ligands of potential utility. The present invention describes a particular strategy for constructing such libraries that provides yet further efficiencies by greatly reducing the physical size of library that needs to be synthesized and tested with the acceptor of interest while still allowing the practitioner to conclude with confidence that the optimal ligand has been identified.

2. BACKGROUND TO THE INVENTION

Those skilled in the art have long recognized the immense effort required to synthesize individually thousands of chemical compounds to be tested for their pharmacologic activity. A potential alternative is to synthesize simultaneously a mixture of millions of compounds in solution which could then be screened in mass to detect the rare compound of potential utility. Methods to generate such mixtures have been described (Rutter, et al. U.S. Pat. No. 5,010,175; Huebner, et al., U.S. Pat. No. 5,182,366), however, the utility of such approaches is greatly limited by the unavoidable fact that as the complexity of a library increases the concentration of any particular species within it decreases. Thus, the task of identifying a compound of interest, present at less than 1 part in $10^5$, and of separating that compound from the other species of library has limited the utility of soluble libraries.

This limitation of the use of random is libraries was largely overcome by libraries constructed using a variety of solid phase synthetic approaches which were then screened while the ligands were still attached to the solid phase supports on which they had been synthesized. Lam and colleagues teach the synthesis on resin particles of random polymer libraries, wherein one species of ligand is present on each particle. Lam et al., 1991, NATURE, 354:82; Patent Publication WO 92/00091. These libraries are constructed by a process termed "split-synthesis," wherein the population of particles is partitioned into as many aliquots as there are species of monomer. Each aliquot is then coupled with a particular species of monomer and, after coupling, all aliquots are recombined and mixed. After synthesis is completed, the ligands are not removed from the solid phase supports as for a soluble library. Rather, Lam teaches that the screening of the library is to be accomplished with the ligands attached to resin or, alternatively, a portion of the ligands may be released from the particle into a corresponding aliquot of test solution. In either case a "positive" resin particle is identified, mechanically isolated and the structure of the potentially useful ligand determined. In an alternative approach, Fodor and colleagues teach the construction of non-random libraries in fixed arrays, using automated chemical synthesis. Fodor et al., 1991, SCIENCE, 251:767–773; U.S. Pat. No. 5,143,854, WO 93/09668. The molecular structure of each ligand in a fixed array library is defined by its location. Thus, while it is more tedious to construct fixed array libraries, they are preferable when the practitioners capabilities to analyze the identified ligands are limited.

Either approach can be very useful and, when the ligand size is small, it is practical to screen all possible ligands constructed from typical sets of monomeric subunits (monomers), for example, the 19 naturally occurring amino acids, excepting cysteine. However, the time and expense of synthesis and screening make economically, if not technically, impracticable the use of libraries having all possible species of larger ligands.

To overcome this impediment, previous workers have attempted to employ libraries containing larger ligands, but ones which are not inconveniently large because they do not contain all possible species or sequences. Such "incomplete" libraries are useful when employed in an iterative procedure: a first generation incomplete library is screened and several "low affinity" ligands are isolated and analyzed. Inspection of the sequences of these several ligands reveals some consensus sequence which is termed a primary motif. A second library is constructed in which the positions defined by the consensus sequence (i.e., the primary motif) and the remaining positions are randomized. Successive iterations can produce ligands having affinities more than 100 fold higher than the primary motif. For example, Lebl et al., 1994, in "INNOVATION AND PERSPECTIVES IN SOLID PHASE SYNTHESIS AND RELATED TECHNOLOGIES," Vol. 3, ed. by Epton, R. isolated a trisodecameric ligand of an anti-insulin monoclonal antibody having an affinity within a factor of 2 of that of the proband protein antigen. The isolation required the successive analysis of the products of four incomplete peptide libraries. By comparison, screening of a complete 13-mer random library, which would contain $20^{13}$ ($8 \times 10^{16}$) species is economically impractical.

Nonetheless the iterative procedure suffers from several shortcomings. Not only must many "special purpose" libraries be synthesized, used once and discarded, but also the procedure requires multiple screenings. More seriously, the second and higher generation libraries are only able to optimize positions that a priori were not within the original consensus and are, hence, evidently less critical in determining the affinity of binding. Thus, the majority of the effort is devoted to optimizing what are apparently the less significant portions of the ligand. Further, the initial search requires the identification of more than one candidate ligands to determine a motif, or alternatively, analogs of an identified ligand must be individually constructed in order to determine the motif.

The present invention is directed towards providing a solution to the problems of efficiently finding the optimal ligand for an acceptor of interest by determining the structure of the optimal primary motif by one screening of a single library. The invention, thus, provides a combination of the practical advantages of a limited library without their deficiencies.

Citation or identification of any reference in Section 2 of this application does not constitute and shall not be construed as an admission by the Applicants that the work described in the reference nor the publication itself was performed, nor that the publication itself was available to the public, prior to the date of the present invention.

3. SUMMARY OF THE INVENTION

The present invention teaches a new type of library of polymers composed of subunits (monomers). The polymers are attached to solid phase supports. Such libraries are useful to identify novel ligands that bind to acceptor molecules, such as enzymes and receptors of all types. By binding, such ligands can alter the function of the acceptor, possessing a utility well understood by medicinal chemists. Ligands that bind without functional effect are useful to label or identify the target acceptor. The present invention differs from the previous types of libraries in that the library is divided into sets. When the library is constructed on individual solid phase particles, each particle bears one set. In a second embodiment, the library may be constructed on a single fixed array of identifiable locations wherein each location bears one set. Although many more than one species of ligand are present in each set, the species of each set are of identical length. Further, each species of the set with all other species of the set shares identical monomers at some positions. A mixture of monomers is present in the set at the other positions. The particular positions and structures of the shared monomers of the set form a motif. The invention teaches that libraries of such sets, hereinafter motif libraries can be used to detect ligands of interest much more efficiently than libraries in which every support carries only a single species of ligand. As ligand size increases so do the advantages of motif libraries.

4. BRIEF DESCRIPTION OF THE FIGURES

FIG. 1. Schematic representation of the flow of intermediate pools to synthesize a complete triplet, hexamer library with the minimum numbers of couplings. An "M" arrow denotes a synthetic step wherein a mixture of all species of monomers is added to every support. An "R" arrow denotes a step of split-synthesis wherein the intermediate is divided into aliquots, one corresponding to each species of monomer monomer, so that any given support has only a single species of monomer at the position. The fractions indicate the ratio of the division of the pool.

Figure 2:
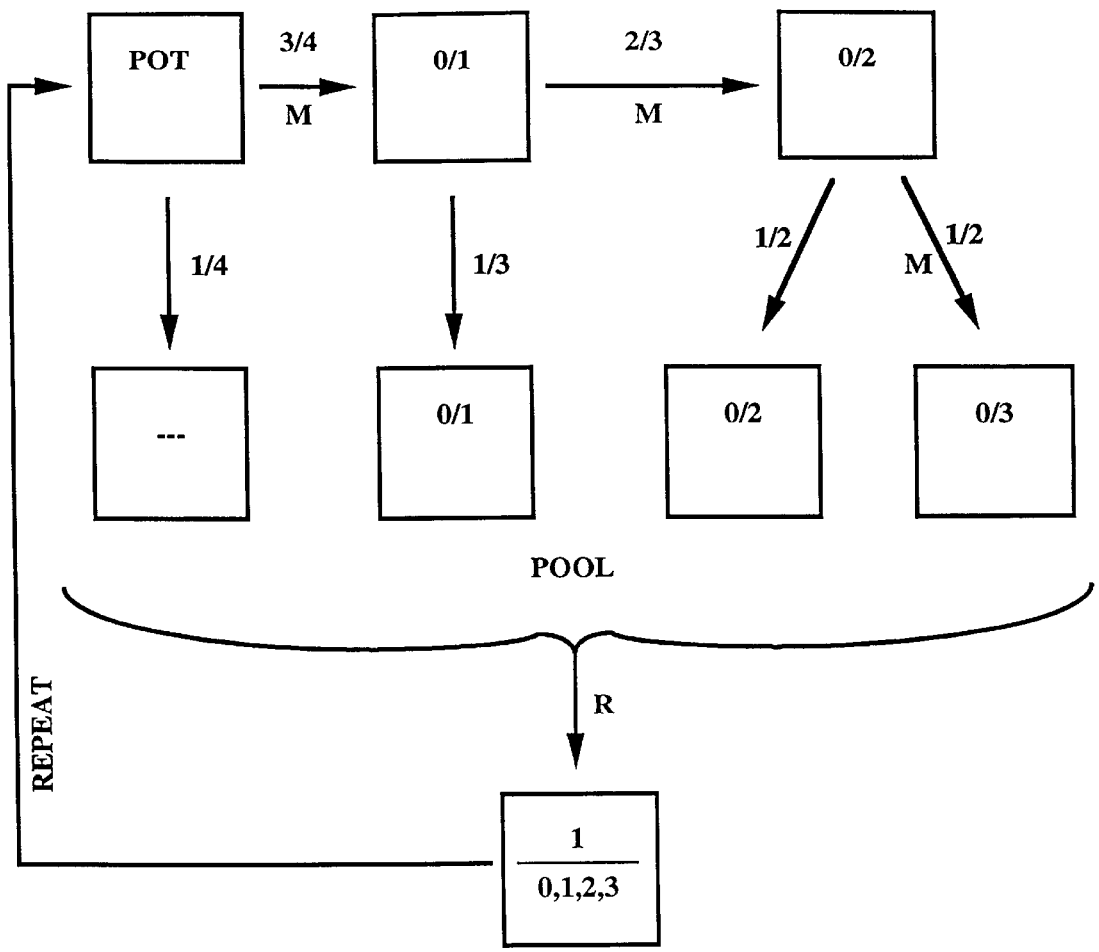

FIG. 2. Schematic representation of the flow of intermediate pools to synthesize a complete random interval library having 0, 1, 2 or 3 residues between each motif position.

5. DETAILED DESCRIPTION OF THE INVENTION GENERAL FEATURES AND DEFINITIONS

The present invention is an improvement equally useful for use with both the solid phase random-type libraries of Lam, Patent Publication WO 92/00091 and the fixed array libraries of Fodor. Fodor, S., et al., 1991, SCIENCE, 251:767–773; U. S. Pat. No. 5,143,854; WO 93/09668. The present invention is based, in part, on the hypothesis that the affinity of the binding of a polymeric ligand to an acceptor is primarily determined by the identity of the residues at a few critical contact positions. Under this hypothesis, the spacing of the contact residues is essential to the affinity of binding, while the particular structure of the residues that occupy the intervening positions of the polymer is not critical. The invention is further based on the realization by the inventors that merely placing some constant, "indifferent" monomer, such as glycine or alanine, at each intervening position would lead to unsatisfactory results because of non-specific effects on binding, alterations in the secondary structure of the ligand and interference by one ligand with the acceptor's binding to neighboring ligands.

The present invention provides for a library of ligands attached to distinct freely mixable solid phase supports or to identifiable portions of a fixed is array type support. The library is divided into sets, each set being attached to a particular support or to a particular position of the fixed array. The library is constructed so that each position of a set is either a motif position or an intervening nonmotif position. At each motif position in a set, there is only a single species of monomeric subunit, while at each nonmotif position at least two different residues are employed and preferably more than 10. Thus, each set contains a very large number of copies of the sequence defined by the motif positions (hereinafter, the motif) and an $S^N$ fold smaller number of each of many different sequences defined by the individual residues at the nonmotif positions, where S is the number of species of monomer and N is the number of nonmotif positions.

The number of motif positions and the number of nonmotif positions can be the same, e.g., a hexamer library of triplet motifs, or the number of nonmotif positions can be significantly larger than number of motif positions, e.g., a dodecamer library of triplet or tetraplet motifs can be used.

The utility of such libraries requires that the binding of acceptor molecules be primarily due to the structure of the motif. Consider, for example, the case of a library of peptides having three nonmotif positions occupied by one of 20 amino acids. For a solid phase particle ~80 μm in diameter, or a fixed array library having locations of the same surface area, there will be ~$10^{10}$ molecules on the surface of each set, each molecule having the same motif. In addition there will be $10^{10}/20^3$ (8,000) (or ~$1.3 \times 10^5$) copies of each of the individual species, each having some particular arrangement of residues at is the nonmotif position. Since most assays can detect as few as 1000 molecules on the surface, it was uncertain, prior to the present teaching whether the binding of an acceptor molecule to such a set would be due primarily to binding to the highly represented motif sequence or whether it would be due to binding to the less frequently represented, but potentially higher affinity ligands, formed by the different combinations of residues at the nonmotif positions. The operability of the present invention depends, in part, on the unpredictable observation that the binding of ligands due to the structure of the motif is not dominated by high affinity binding to other sequences in the set.

The invention, thus, provides for libraries composed not of individual polymer sequences but of individual polymer motifs and teaches, for the first time, that activity of the motifs as ligands can be screened-for in the same manner as the ligand activity of individual polymer species.

The invention further provides two particular embodiments of motif libraries. The first embodiment provides a library consisting, in approximately equal amounts, of all permutations of a predetermined number of motif and nonmotif positions. There are, for example, 20 different sequences of motif and nonmotif positions in a triplet, hexamer library. Thus a triplet, hexamer library composed of all the natural amino acids would contain 160,000 different motifs. By contrast a complete, natural amino acid, hexamer library contains $6.4 \times 10^7$ peptide sequences. It would require several times that number of individual supports to ensure that all sequences were represented.

The second embodiment recognizes that the practitioner most frequently is unable to predict with confidence the number of motif and non-motif positions in the library in which the most desired ligands can be found. Thus, although she can reasonably desire, for example, to examine all hexamer triplets, there would not often be a strong reason to exclude motifs other sizes. Thus, the second embodiment considerably simplifies the task of construction by providing a library having a all possible motif sequences of a predetermined size and in addition a large number of related sequences having a varying numbers of nonmotif positions. While the library so constructed contains sequences of variable length, each set within the library has a single characteristic number of nonmotif positions.

The invention encompasses polymers wherein the monomers are covalently connected by every sort of chemical bond which those skilled in the art will recognize can be synthesized on a solid phase support. The term polymer as used herein includes those compounds conventionally called heteropolymers, i.e., arbitrarily large molecules composed of varying monomers, wherein the monomers are linked by means of a repeating chemical bond or structure. The polymers of the invention of this type are composed of subunits or monomers that can include any bi-functional organic or herteronuclear molecule including, but not limited to amino acids, amino hydroxyls, amino isocyanates, diamines, hydroxycarboxylic acids, oxycarbonylcarboxylic acids, aminoaldehydyes, nitroamines and thioalkyls and haloalkyls having one of the previously noted functionalities. The monomers of the test ligand are linked by chemical bonds selected from the group consisting of amide, ester, urea, urethane, carbonate, amine, alkane, alkene, sulfide, and disulfide. A monomeric subunit can also be comprised of additional functionalities which are not used in the synthesis of the polymer, as for example the $\epsilon$-amino group of lysine. The various chemistries which are within the scope of the present invention are described in co-pending, co-assigned U.S. patent applications Ser. No. 068,327, filed May 27, 1993, which is hereby incorporated by reference in its entirety.

In the present invention, the polymer is connected to the solid phase support by means of a linker. As used herein the term "linker" refers to, at least, the most distal atom of the solid phase support to which the monomers of the polymer is attached and can also include larger chemical structures that are identical in all the species of ligands of the library. Linkers can be used to provide physical separation between the ligand and the solid phase support. The term linker also includes structures, hereinafter called molecular scaffolds, which are a special type of linker having a plurality of reactive moieties to which monomers can be attached and which provides some of the specific structure of the ligand. The subunits attached to the scaffolds, which are also termed monomers, can be either monofunctional or bifunctional. In the case of monofunctional monomers the resultant test ligand consists of the molecular scaffold to which it is attached, in radial fashion, a limited number of monomers. In the case wherein bifunctional monomers are employed the ligand consists of the molecular scaffold and a variable, potentially unbounded number of multimers attached in radial fashion to the scaffold. As used herein the term "polymer" is intended to include both of the above-described radial molecules consisting of the scaffold and monofunctional and/or bifunctional monomers as well as the above-described heteropolymers.

The term "monomer species," as used herein, refers to the individual specific structure of a particular monomer and also, when used to define a motif position, refers to a collection of chemically homologous monomers which those skilled in the art would expect to have nearly equivalent properties under the particular circumstances. Thus, in some circumstances glycine and alanine or lysine and ornithine are each be considered a one monomer species when used at a motif position.

The solid phase support can be either a bead, i.e., a physically distinct, freely mixable particle, or the support can be in a fixed array of pins or vessel walls or it can be a fixed array of locations on an otherwise undifferentiated surface. The library can be screened in either of two basic modes, which are more fully described by Lam et al. Patent Publication WO 92/00091. In the first mode, the test ligands remain attached at all times to the solid phase support(s), to which is added a soluble acceptor of interest. The binding of the acceptor or interest is detected by suitable second and third step reagents which label support(s) having active ligands. Under the proper circumstances, it can be necessary to provide the soluble acceptor molecules in multimeric form by, for example, biotin conjugation and avidin cross-linking, whereby the avidity of binding between the ligand and the acceptor is increased.

Binding to a particular portion of an acceptor, e.g., an active site of an enzyme, can be detected by a two phase process, whereby, in the first phase binding to the acceptor per se is detected and the thusly labeled supports identified and/or isolated. In the second phase, a blocking molecule is added, which binds to the particular portion of the soluble acceptor, e.g., a competitive inhibitor of the enzyme. The motifs that bind the acceptor in the first phase but not in the second are, thus, the ligands which bind to the particular portion of interest.

A second type of screening assay is useful when the acceptor is present in a living cell and the practitioner desires to measure the effects of binding on the cell. The test ligands are connected to freely mixable solid phase supports by a selectively and controllably cleavable linker. The test ligands are released from the supports under conditions wherein the effects of ligands released by a particular individual support or a small group of supports can be identified. To this end the supports can be placed in a plaque or replica-plating assay or they can be divided into a multitude of portions, for example, in 8×12 microculture arrays. By observing the effects of the soluble ligand, the support that released the ligand of interest can be identified and isolated. The chemistries suitable to construct cleavable linkers are explained in detail in co-pending, co-assigned U.S. patent application Ser. No. 5 081,997, filed Jun. 23, 1993, which is hereby incorporated by reference in its entirety.

After completion of the screening assays and isolation and/or identification of the support of interest, the structure of the ligand may be determined by a variety of means well understood by those skilled in the art. When the test ligand is a peptide polymer its structure may be analyzed directly by conventional Edman degradation. Peptides, as well as many polymers that cannot be sequenced by Edman degradation, can be analyzed by mass spectrometry. Under certain circumstances, the practitioner may desire only to identify the composition of the monomers of the motif positions. When the number of nonmotif positions divided by the number species of monomer subunits at each nonmotif position is much less than one, this goal can be accomplished merely by hydrolysis of the ligands and analysis of the products.

An alternative embodiment within the scope of the invention contemplates the use of a coding molecule, that are readily sequencable, to represent the structure of the motif of a test ligand that can then be itself non-sequencable. To avoid inadvertently detecting the binding activity of the coding molecule, it is preferable to have the coding molecule topologically separated from the test ligands. Such can be accomplished by enzymatically shaving the solid phase support so as to differentially expose the "surface" and the "interior." Vagner et al., 1993, "Novel Methodology for Differentiation of "Surface" and "Interior" . . ." in "INNOVATION AND PERSPECTIVES IN SOLID PHASE SYNTHESIS AND RELATED TECHNOLOGIES" ed. by Epton, R.; U.S. patent application Ser. No. 068,327, filed May 27, 1993. When a release assay is employed, the topological separation is easily accomplished by attaching the coding molecule by means of a non- cleavable linker.

The term coding molecule as used herein refers to a molecule or a set of different molecules that are attached to a solid phase support and can be analyzed so as to reveal the structure and/or composition of the motif of the solid phase support. Thus, a "coding molecule" can be a single sequencable polymer or a plurality of such polymers, wherein the code resides in both the composition and the sequence(s) of the coding molecule. Alternatively, the coding molecule may consist of a non-sequencable branched polymer or any other set of chemical moieties, the monomers of which can be covalently connected directly to each other or connected only through the solid support, so long as the analysis of the composition of coding molecule reveals the structure and/or composition of the motif. Coding molecules and a detailed description of their use is provided in the above-noted co-pending, co-assigned U.S. patent applications Ser. No. 068,327, filed May 27, 1993.

5.1 TECHNIQUES OF SYNTHESIS

5.1.1 SYNTHESIS OF MOTIF POSITIONS

Motif Positions are synthesized as taught by Lam, et al., Patent Publication WO 92/00091; Huebner, et al., U.S. Pat. No. 5,182,377 and Furka, et al., 1988, 14th International Congress on Biochemistry, Prague, Czechoslovakia, 5:47; 1988, 10th International Symposium on Medical chemistry, Budapest, Hungary, p. 288.; Furka, A., et al., 1991, INT. J. PEPTIDE PROTEIN RES. 37:487.

5.1.2 SYNTHESIS OF NONMOTIF POSITIONS

The present invention requires that there be a plurality and preferably a multiplicity of monomeric species at the nonmotif positions. It is not critical that the individual species be present in exactly equimolar amounts. In the preferred embodiments the ratio of the most to least prevalent species at the nonmotif positions will be less than about 8; more preferably less than 4 and most preferably less than between 1.5 and 2.5. Variations in the representation of monomers of less than a factor of 1.5 are not expected to be significant. For some collections of species of monomers, hereinafter the species alphabet, these requirements can be achieved by the simple expedient of adding equimolar concentrations of the various species. More often the practitioner will be required to test the particular alphabet to determine whether some adjustment is required for the differences in the rate of coupling of the different species. Those skilled in the art will recognize that such relative rates can be determined with sufficient accuracy for the practice of the invention merely by coupling an equimolar mixture of the alphabet to the supports wherein the concentration of reactive sites on the supports is in excess of that of the total concentration of monomers.

Should it be necessary to compensate for the inequalities in the coupling rate there are two strategies available. In the first the mixed coupling is performed in two stages. In the first stage the reaction mixture consists of an equimolar mixture of the species of the alphabet, in which the total amount of monomers is about 0.8 that of the total amount of reactive sites on the support which are to be coupled. Andrews et al., 1994, TECHNIQUES IN PROTEIN CHEMISTRY, 5:485–492. The differences in the rate of the reaction of the monomers is thus irrelevant under these circumstances wherein all reactions are expected to go to substantial completion. In the second stage, a second equimolar mixture may be added to complete the coupling of the remaining reactive sites on the supports, the numbers of which are too few to compromise the functionality of the library.

The second approach to compensate for the differences in the reaction rates of the monomers requires that the ratio of the monomers be adjusted in roughly inverse proportion to the relative differences in their rates of reaction, which are determined as noted above. Rutter et al.; U.S. Pat. No. 5,010,175; Andrews et al., 1994, TECHNIQUES IN PROTEIN CHEMISTRY, 5:485–492.

5.1.3 THE SYNTHESIS OF A COMPLETE MOTIF LIBRARY

The synthesis of a motif library can, in theory, be accomplished by performing, in all permutations of the desired number of steps of mixed synthesis and split synthesis, using the desired species alphabet at each step, that correspond to the desired number of nonmotif and motif positions. Libraries in which all sets of test ligands have the same numbers of motif and nonmotif positions are called herein "defined parameter libraries." Thus, for example a hexamer, triplet defined parameter library can be synthesized by the 20 different permutations of two items taken three at a time; requiring 120 individual synthetic steps. Considerable savings can be obtained, however, by following a more complex pattern of poolings and splittings whereby the total number of synthetic steps is reduced to 24, i.e., 12 mixed syntheses and 12 random syntheses or split syntheses. This pattern is expressly illustrated for the hexamer, triplet, library in FIG. 1.

In FIG. 1, each intermediate pool is given a status designation, e.g., 211, which indicates the number of motif positions and nonmotif positions which have been coupled, and a history designation, e.g., XXRM, which indicates whether a given position in the pool is the result of a random split synthesis (R), i.e. a motif position, or the result of a mixed synthesis (M) and thus a nonmotif position. When two separate intermediates have been pooled so that both M and R are present at a particular position an X is designated. In this notation the completed pooled hexamer, triplet, library is designated the 3/3 XXXXXX pool.

The flow pattern is constructed by following two rules. Firstly, intermediates having the same status are combined because the subsequent treatment of any intermediate pool depends solely on the number of motif and nonmotif positions already present; the order of the previous steps is irrelevant to the numbers of each type of step remaining to be performed. Secondly, the pools are divided between the next R step and the next M step in the ratio of the steps of each type that are required to complete the synthesis. Thus, for example, the 2/1 XXX pool requires 1 additional R step and 2 additional steps. Therefore, it is divided so that 2/3 of the total goes into an M synthesis to make a 2/2 XXXM pool and 1/3 into an R synthesis to make a 3/1 XXXR pool. Similarly the 1/0 R pool, which requires 3M steps and 2 R steps to complete, is divided 3/5 into M for the next step and 2/5 into R for the next step. Those of ordinary skill will appreciate that the above described rules provide guidance which enables the efficient construction of defined parameter libraries having any number of motif and nonmotif positions.

5.1.4 THE SYNTHESIS OF VARIABLE INTERVAL LIBRARIES

Although defined parameter libraries of any size can be synthesized by the above scheme, those larger than a hexamer, triplet library become evidently tedious to construct because of the necessity of tracking, mixing and dividing many individual intermediate pools. A second embodiment of the invention is provided whereby motif libraries can be synthesized without incurring the complexities necessitated by the syntheses of defined parameter libraries. This method of synthesis is more appropriate for the construction of heteropolymers. The synthesis of polymers using molecular scaffolds having only monofunctional monomers is not possible by this method. A disadvantage of variable interval libraries is that they may be encoded only with sequential codes.

This method of synthesis provides libraries in which there are a constant number of motif positions which are separated by nonmotif positions of randomly variable length up to some predefined length. Each set of ligands of library has, however, the same number of nonmotif positions. Such a library is termed a "variable interval library." Thus, for example, a so-called triplet, trimmer variable interval library contains sets having all the 20 permutations of Rs and Ms contained in the hexamer, triplet defined parameter library and also contains polymers of the form RRR and MMMR-RRMMM up to the 15-mer MMMRMMMRMMMRMMM. A triplet trimmer variable interval library would contain 256 permutations of motif and nonmotif positions.

The scheme whereby such libraries having trimmer intervals can be synthesized is illustrated in FIG. 2. A library having up to N nonmotif positions between each motif position is synthesized by dividing the working mass of solid phase supports into fractions of 1/N+1 and N/N+1; the former is reserved, the latter is placed into a mixed synthesis step. The pool from the mixed synthesis step is then divided into a reserved fraction of 1/N and a working fraction of N−1/N which is placed into a second synthesis step. The scheme is continued until the last pool is split equally into the reserve and working fractions. All fractions are then pooled and a random split synthesis step is performed after which the process is repeated. Certain economies of material can be achieved by synthesizing the library in N+1 separate procedures so that the sum of number of nonmotif position added before the first motif position and after the last motif position is constant.

5.2 CHEMISTRIES USEFUL IN THE CONSTRUCTION OF THE LIBRARIES

The present invention contemplates the use of any chemistry which is compatible with synthesis on a solid phase support. Synthetic solid phase supports which are useful in the practice of the invention are silica gels, resins, derivatized plastic films, glass beads, cotton, plastic beads, and polysaccharides. Useful chemistries of resins include polystyrene, polyamide, polydimethylacrylamide, polyamide, and polystyrene resin grafted with polyethylene glycol.

The present invention contemplates the use of peptide chemistry to provide both the test ligands and the coding molecules. Additional types of chemistries may be used to link the monomers of the test ligand which produce polyureas, polyurethanes, polyesters, polyethers, polycarbonates, polyamines, polyalkanes, polysulfides, polydisulfides, or polymers containing any combination of such bonds.

The ligands may also include a molecular scaffold having various substituents at defined positions, in which the scaffold can be a cyclic or bicyclic hydrocarbon, a steroid, a sugar, a heterocyclic structure, or a polycyclic aromatic molecule. The scaffold can be derivatized by monomers using the same chemistries as can be used to construct the above noted polymers. When the monomers are monofunctional the derivatized scaffold forms a polymer of inherently defined length. When bifunctional monomers are used multiple polymers of arbitrary length can be constructed, which are all attached to the solid phase support through the scaffold.

5.3 METHODS OF DETECTION

The present invention allows identification of ligands that bind acceptor molecules. As used herein, the term "acceptor molecule" refers to any substance which binds to a ligand. Acceptor molecules may be a biologic macromolecule such as, but not limited to, antibodies, receptors, or viruses.

The motif library of the invention can potentially interact with many different acceptor molecules. By identifying the particular ligand species to which a specific acceptor molecule binds, it is possible to physically isolate the ligand species of interest.

Because only a small number of species of motif will be removed during each screening/detection/isolation step, the majority of the beads will remain in the pool. Therefore, the library can be reused multiple times. If different color or identification schemes are used for different acceptor molecules (e.g., with fluorescent reporting groups such as fluorescein (green), Texas Red (Red) and DAPI (blue) tagged on the acceptors), and with suitable excitation filters in the fluorescence microscope or the fluorescence detector, different acceptors (receptors) can be added to a peptide library and evaluated simultaneously to facilitate rapid screening for specific ligands. These strategies not only reduce cost, but also increase the number of acceptor molecules that can be screened.

In the method of the invention, an acceptor molecule of interest is introduced to the library of bio-oligomers where it will recognize and bind to one or more ligand species within the library. Each ligand species to which the acceptor molecule binds will be found on a single solid phase support so that the support, and thus the bio-oligomer, can be readily identified and isolated.

The support can be isolated by any conventional means known to those of ordinary skill in the art and the invention is not limited by the method of isolation. For example and not by way of limitation, it is possible to physically isolate a solid phase support/ligand combination that exhibits the strongest physico-chemical interaction with the specific acceptor molecule. In one embodiment based on physico-chemical interaction, a solution of a specific acceptor molecule added to a random peptide library which is equivalent to approximately $10^5$ to $10^7$ solid phase supports. The acceptor molecule is incubated with the resin for a time sufficient to allow coupling between the peptide and antibody, for example, one hour at 22° C. Thereafter, the acceptor molecule coated bio-oligomer/solid phase support is isolated. More specific embodiments are set forth below. Although the following refers to libraries of peptides, it will be understood that motif libraries of having other chemistries may also be assayed.

Binding to a specific portion of an acceptor may be determined. After the isolation of the supports, the precipitated dye may be removed by washing in any suitable organic solvent. The cleanly washed supports are not reexposed to the same acceptor, but with an "inhibitor" known to bind to the portion of interest. Supports that now fail to bind are selected and stained yet again in the absence of inhibitor. The desired supports are those that stain in the first and third but not second exposures.

(i) The acceptor is first labeled with a fluorescent moiety or "fluoresceinated" by techniques that are within the routine skill of those in this art. The antibody at a concentration of 1 ug/ml is then introduced to the library of peptides and, after gentle mixing at 22° C. for one hour, the solid phase supports are washed, and the fluorescent antibody solid phase support/peptide combinations are identified and recovered with a fluorescence activated cell sorter. Alternatively, the fluorescent antibody solid phase support/peptide combinations are identified and physically picked up under a dissecting microscope with fluorescent attachment using a micromanipulator. The relative intensity of fluorescence is generally proportional to the affinity of the peptide-ligand to the monoclonal antibody in question.

(ii) The acceptor is first conjugated onto ferro-magnetic beads by techniques that are routine in the art. The conjugated antibody at a concentration of 1 ug/ml is then incubated with the library for one hour at 22° C. The magnetic beads will form a rosette around the solid phase support/peptide of interest which can then be physically isolated with a strong magnet.

(iii) The acceptor is first conjugated is to an enzyme such as alkaline phosphatase by techniques that are routine in the art. This antibody-enzyme conjugate is then incubated with the random peptide library for 30 minutes to one hour at 22° C. After washing, the whole library is poured into a petri dish which contains a substrate for alkaline phosphatase, for example, 5-bromo-4-chloro-3-indoyl phosphate (BCIP) and nitro-blue tetrazoleum (NBT). After incubating for several minutes, the antibody-solid phase support/peptide combination changes color (becomes blue) due to precipitation of the converted substrate on the solid phase support, and can be easily identified and isolated physically under a dissecting microscope with a micromanipulator. The relative intensity of the color reaction is generally proportional to the affinity of the peptide for the monoclonal antibody in question.

(iv) The acceptor is first conjugated to an enzyme such as horseradish peroxidase by techniques that are routine in the art. This antibody-enzyme conjugate is then incubated with the random peptide library for 30 minutes to one hour at 22° C. After washing, the whole library is poured into a petri dish which contains a substrate for peroxidase, for example, 3,3',4,4'-diaminobenzidine (DAB); 3,3',5,5'-tetramethylbenzidine (TMB); or 4-chloro-1-napthol (4CN). After incubating for several minutes, the antibody-solid phase support/peptide combination changes color, and can be identified and isolated physically under a dissecting microscope with a micromanipulator. The relative intensity of the color reaction is generally proportional to the affinity of the peptide for the monoclonal antibody in question.

(v) The acceptor is first labeled with biotin or "biotinylated" by techniques that are routine in the art and is thereafter incubated with the random peptide library for 30 minutes to one hour at 22° C. After washing, a streptavidin-alkaline phosphatase or streptavidin-horseradish peroxidase complex is added and incubated for 30 minutes. The support is then washed, and the color is developed as described above in (iii) with the enzyme method. The peptide/solid phase support of interest is physically isolated as above.

The instant invention further provides assays for biological activity of a ligand from a library. The biological activities that may be assayed include toxicity and killing, stimulation and growth promotion, and physiological change.

In a preferred embodiment, the bio-oligomers of the library are selectively cleavable from the solid-phase support, also referred to herein as "bead". In one embodiment, beads are prepared such that only a fraction of bio-oligomers are selectively cleavable. A library is treated with a cleaving agent such that cleavage of a fraction of bio-oligomers occurs. Examples of cleaving agents include, but are not limited to, UV light, acid, base, enzyme, or catalyst.

Since the beads of the library are immobilized, a concentration gradient of a particular ligand will form. High concentrations of ligand will be found in proximity of the bead from which it was released. Thus, evidence of biological activity of interest, in proximity to a bead, will allow identification and isolation of the bead, and sequencing or other characterization of the bio-oligomer. In another embodiment, the beads may be partitioned in microtiter wells (e.g., 10 beads/well) and a percent of ligand released and tested for biological activity, thus eliminating the potential problem of diffusion. As described below, different fractions of ligand may be attached to solid phase support or bead via different cleavable linkers for sequential assays. Within these examples, the term "bead" refers to solid phase support.

5.4 METHODS OF DETERMINATION OF THE STRUCTURE OF THE LIGANDS

Once a support containing a ligand of interest is selected according to any one of the methods of Section 5.3., supra, the present invention provides a means of determining the structure of the ligand.

There are two general approaches to determining the structure of a motif: the structure of the polymer may be directly analyzed by conventional techniques, e.g., Edman degradation or mass spectrometry; alternatively, a second molecule or group of molecules may be synthesized during the construction of the library such that the structure(s) of the second molecular species unambiguously indicates (encodes) the structure of the motif attached to the same support. By this second technique, the structure of polymers that are not themselves amenable to sequencing can be readily determined. The present invention also teaches a third technique, term "fractional coding" whereby specific monomers that are not resolvable in conventional analysis, e.g., D and L stereo isomers, can be distinguished by adding a small amount of a monomer not otherwise utilized in the construction of the library. The practice of fractional coding creates a minor degree of heterogeneity at the motif positions of the ligand. For the purposes of the present invention such a degree of heterogeneity, typically 5%, is compatible with the designation of the position as a motif position.

5.4.1 CHARACTERIZATION OF THE LIGAND BY DIRECT MEANS

For the analysis of the structure of ligands selected from libraries which do not contain coding molecules, the technique used to analyze the structure of coding peptides (described below) may be used when applicable. Alternatively, mass spectrometry particularly using techniques described in U.S. application Ser. No. 081,977 filed Jun. 23, 1993 or other analytical techniques (thin layer chromatography, HPLC, NMR, IR, elemental analysis, and the like) can be used to determine the structure of a synthetic test compound selected according to the present invention.

5.4.2 CHARACTERIZATION BY MEANS OF SINGLE AND MULTIPLE SEQUENTIAL CODES

In an alternative embodiment of the present invention, each solid phase support containing the motif also contains a molecule, preferably a peptide whose sequence encodes the structure of the motif, i.e., determination of the sequence of the coding peptide reveals the identity of the ligand. A preferred method of coding peptide sequencing is Edman degradation. A particularly preferred method employs the Applied Biosystems 477A Protein Sequencer. The amino acid sequence of peptides can also be determined either by fast atom bombardment mass spectrometry (FAB-MS) or using other analytical techniques.

The coding peptides can be sequenced either attached to or cleaved from the solid support. To cleave the peptides, the isolated beads are treated with traditional cleaving agents known to those of skill in this art to separate peptides from solid phase supports. The choice of cleaving agent selected will depend on the solid phase support employed.

Alternatively, in another embodiment within the scope of the invention, it is possible to isolate a single solid phase support particle, such as a bead, with its coding peptide sequence attached and introduce the bead to a sequencer for peptide sequencing without previously cleaving the coding peptide from the bead. It is estimated that a single 100 $\mu$m diameter resin bead with 0.5 mEq/gram of functionalizable sites contains approximately 100 pmole of peptide if one half of the sites are used to link coding peptides. For a similar degree of substitution with coding peptides, a single 250 $\mu$m diameter PAM resin bead with 0.5 mEq/gram resin of functionalizable sites contains approximately 1500 pmole of coding peptide. With state of the art peptide sequencer, only 5–10 pmole is required for adequate sequencing. Therefore, for a standard PAM resin a single bead of 100 $\mu$m in diameter can be loaded to contain more than an adequate amount of coding peptide for sequencing.

In addition to Edman sequencing, fast ion bombardment mass spectrometry is a very powerful analytical tool and can often be used effectively to analyze the structures of peptides and of a variety of other molecules. Electrospray-high performance mass spectrometry can also be very useful in structural analysis. Preferably, mass spectrometry to determine the structure of a coding molecule is performed as described in co-pending, co-assigned U.S. patent application Ser. No. 081,977 filed Jun. 23, 1993.

Once the structure of a selected ligand is determined, a large amount of the compound can be synthesized chemically or biologically for confirmation of the results of the structural and screening experiments and other studies.

Those skilled in the art will appreciate that at times the number of species of monomers at any position of the test compound is larger than the number of types of monomers used to construct the coding polymer. For example, a coding peptide can be constructed with a limited set of amino acids that are readily distinguished after Edman degradation. Under these circumstances the coding molecule can be constructed by introducing a mixture of amino acids at a given position. For example a singlet/doublet code, i.e., having one or two coding moieties per position of the test compound, in which the coding polypeptide contains only 8 amino acids can encode up to 36 monomers; a triplet/doublet/singlet code with the same number of moieties encodes 84 subunits per position.

The analysis of the Edman degradation products of such coding peptides will reveal either one or two, or one, two or three amino acids at each position of the coding sequence.

5.4.3 CHARACTERIZATION BY MEANS OF A NON-SEQUENTIAL CODE

In an alternative embodiment, the reading of the coding molecule does not require knowledge of the sequence of its subunits. Sequential codes are inherently laborious to decode. Sequencing of a molecule requires reiterated degradative steps, by contrast analysis of the composition of a polymeric molecule can be performed in a single degradation and single analysis of the resultant subunits or their derivatives. Further, the slowest part of sequencing of peptide coding molecules is the chromatographic analysis of each of the cleaved phenylthiohydantoins because most of the time of gradient analysis is "wasted". All the information resides in the unique retention time of the single eluted peak. If instead of sequential Edman degradation followed by HPLC analysis, it were possible to simultaneously cleave all the coding subunits, distinguish between them in a single HPLC run, and then decode the results to determine the test compound identity, the process could be greatly accelerated.

Reading a non-sequential code requires only determining whether a given signal is present or not. The baseline resolution of two peaks which differ by about 0.3 minutes in retention time can be achieved using the standard reversed phase HPLC analysis with gradient elution. Therefore, a 45 minute gradient can discrimate among 150 compounds. A coding molecule consisting of subunits selected from a group of 150 different coding moieties is equivalent to a 150 digit binary number. Hence, $2^{150}$ or about $10^{45}$ different species of test compound could be so encoded. Thus, non-sequential codes are easily adequate to encode both the sequence and the identity of the monomers of the test compounds of even the largest practical libraries.

A non-sequential code can be constructed as follows. Let C000 to C099 be the elements of the set of 100 coding moieties to be used to encode the structure of a test compound having up to 20 residues selected from up to 32 different monomers, called here S00-S31. In this scheme the identity of the residue at the first position is determined by the presence or absence of coding moieties C000–C004; if none are present S00 is present at the first position of the test compound, if all are present S31 is present at position 1. Successive positions are encoded by moieties C005–C009, C010–C014 . . . C095–C099. Those of ordinary skill will understand that, in the frequent case wherein libraries considerably smaller than the maximum coding capacity of a 100 digit code are required; the fidelity of the code may be increased by either reducing the size of the set of coding molecules, i.e., increasing the interval between moieties in the chromatographic analysis, or by the use of redundant coding, e.g., a "parity" moiety may be introduced into the code for each encoded position.

Most frequently, between 4 and 8 coding moieties, corresponding to between 16 monomers and 128 monomers plus a parity moiety, will be required to encode each position in the test compound.

The coding moieties need to be arranged in the coding structure to allow their simultaneous cleavage and analysis. One obvious possibility is total hydrolysis, followed by selective modification and analysis of the mixture. In this case the structure of the coding compound is not important. Coding moieties can be connected to one another, or attached to separate branches of a branched structure, or any combination so long as the bond to each moiety is hydrolyzable. This approach, however, might be compromised by the presence of hydrolytic products from the test compound. Therefore, the use of the very selective degradation method designed by Edman, 1950, ACTA CHEM SCAND, 4:283–293; Edman, et al., 1967, EURO J BIOCHEM, 1:80–91 seemed the optimal choice.

Edman degradation selectively cleaves the N-terminal amino acid from the peptide chain. If a reasonable number of amino acids and amino acid derivatives fulfilling the chromatographic requirements defined above could be identified, and they were synthesized as a coding structure in an arrangement allowing their simultaneous cleavage, it would be possible to analyze the composition of a nonpeptidic structure in just one cycle of Edman degradation and HPLC analysis.

The retention time of amino acid phenylthiohydantoins on reversed phase follows the lipophilicity of the side chain of the amino acid. Thus, to design a set of amino acid derivatives with the appropriate retention times it is only necessary to design the side chain of each with appropriate differences in lipophilicity. One simple way to achieve the appropriate differences is to substitute the functional group of the side chains of trifunctional amino acids by appropriate substituents. Consequently, we explored the effect of acylating the side chain amino group of diamino carboxylic acids—diaminopropionic acid, diaminobutyric acid, ornithine and lysine. The set of carboxylic acids used is given in Table I together with the results of HPLC analysis of the prepared phenylthiohydantoin analogs. The gradient used in the automatic sequencer was modified. Even though this linear gradient (8 to 90% acetonitrile in 0.01M NaOAc buffer in 42 minutes) did not separate some natural amino acids (leucine and lysine), it separated most of the newly designed diamino carboxylic acid derivatives with high is reproducibility. The retention times of all prepared compounds together with the retention times of some natural and unnatural amino acids can be ascertained by those skilled in the art. Alternative sets of coding moieties will be readily apparent to those skilled in the art. The above described moiety is preferred only in that it can be conveniently synthesized by those having ready access to solid phase peptide synthesis.

TABLE I.

| Species No. | α,β- Diamino proprionic Acid | α, γ- Diamino bulyric Acid | ornithine | lysine | Derivative |
|---|---|---|---|---|---|
| 1 | * | * | * | * | acetyl |
| 2 | * | * | * | * | propionyl |
| 3 | * | * | * | * | butyryl |
| 4 | * | * | * | * | valeryl |
| 5 | * | * | * | * | caproyl |
| 6 | * | * | * | * | pivaloyl |
| 7 |  | * | * | * | c-hexyl |
| 8 |  | * | * | * | trichloroacetyl |
| 10 |  | * | * | * | phenylacetyl |
| 11 |  | * | * | * | 2,2-diphenylacetyl |
| 12 |  | * | * | * | phenylbutyryl |
| 13 |  | * | * | * | 1-naphtylacetyl |
| 14 |  | * | * | * | 2-naphtylacetyl |
| 15 | * | * | * | * | 1-adamantyl-carbonyl |
| 16 |  | * | * | * | 1-adamantylacetyl |
| 17 |  | * | * | * | tosylglycyl |
| 18 |  | * | * | * | dansylglycyl |
| 19 | * | * | * | * | beiizoyi |
| 20 | * | * | * | * | succinamyl |
| 21 |  | * | * | * | succinyl |
| 22 |  | * | * | * | glutaryl |
| 23 | * | * | * | * | isobutyryl |
| 24 |  | * | * | * | 4-chlorobenzoyl |
| 25 |  | * | * | * | 2,2-diphenylpropionyl |
| 26 |  | * | * | * | N,N-dimethylglycyl |
| 27 | * | * | * | ** | heptanoyl |
| 28 | * | * | * | * | octanoyl |
| 29 | * | * | * | * | 3,3-di-ph-propionyl |
| 30 |  | * | * | * | N,N-dimethylamino butytyl |
| 31 | * | * | * | * | 3-ph-propionyl |
| 32 | * | * | * | * | 4-bi-ph-carbonyl |
| 33 | * | * | * | * | 4-bi-ph-acetyl |
| 34 | * | * | * | * | crotonyl |

One embodiment to achieve the simultaneous cleavage of coding moieties provides that every coding moiety is an α-amino acid, attached as an N-terminal amino acid with its amino group free. The backbone of the coding structure is constructed from diamino carboxylic acids (Daa). The amino groups of these amino acids are acylated by the N-protected amino acids used for the coding. Acylation is performed using a mixture of the moieties defined as a code for the given monomer and its position in the test compound.

In the case of the substituted diamino carboxylic acids described in Table I, the coupling reactivities are independent of side chain substitutions.

There are several basic strategies for the construction of a coding molecule as described above. The first is based on the use of the Alloc protecting group (Loffet et al., 1993, INT J PEPTIDE PROTEIN RES, 42:346–351); (Stevens, et al., 1950, J AM CHEM Soc, 72:725–727); (Guibe et al., 1981, TET LETT, 21:3591–3594) for building the coding structure and the Fmoc or Fmoc-like group (Carpino et al., 1972, J ORG CHEM, 37:3404) for the protection of functional groups on the test compound. In this case the Boc group can be used as the permanent protecting group for both the test compound synthesis and coding synthesis. It is advantageous to use preformed coding subunits. Alternatively, if preformed coding subunits are not used, another level of orthogonality is required during synthesis. This can be achieved by using Alloc/Ddz protected diamino carboxylic acids for building the coding backbone. Since the Ddz group is selectively cleavable by 2% trifluoroacetic acid in dichloromethane (Birr et al., 1972, LIEBIG's ANN CHEM, is 763:162–173). However, this approach is complicated by the need to compensate for different coupling reactivities of the coding amino acids attached as a mixture. The second strategy is based on the use of a combination of Fmoc and Boc groups for temporary orthogonal protection of functional groups in the test compound and coding molecules, and the use of benzoxycarbonyl (Z) or Z-like groups for permanent protection. The coding subunit can be built during the synthesis using Fmoc/Dde (or Fmoc/Alloc, or Fmoc/Ddz) protected diamino carboxylic acids since the Dde group is cleaved by a solution of hydrazine in dimethylformamide and is stable under conditions used for removal of the Boc or Fmoc group (Hone et al., 1992, Poster P63 at 22nd Eur Pept Symp, Interlaken, Switzerland).

Alternatively coding may be provided by allowing a fraction of the amino groups, available for coding, to be acylated by a coding mixture; the remaining amino groups are then reprotected by orthogonally cleavable group (e.g. Alloc) before the next step of randomization is performed. In this scheme the individual subunits of the coding sequence are attached directly to the solid phase support and are not a part of a polymer. In this scheme it is advantageous to couple the coding mixture prior to the test compound monomer since the deprotection of Alloc can be performed in the recombined stage.

6. WORKING EXAMPLES

6.1 PROCEDURES FOR SYNTHESIS OF SOLUBLE PEPTIDES

Starting materials used in the synthesis were obtained from research grade chemical vendors such as Aldrich, Sigma, Fluka, Nova Biochem and Advance Chemtech. During the synthesis of the peptides and libraries, the functional groups of the amino acid derivatives were protected by blocking groups, to prevent side reaction during the coupling steps. Examples of suitable protecting groups, and their use are described in "The Peptides: Analysis, Synthesis, Biology", Academic Press, Vol. 3, E. Gross & Meienhofer edit. 1981, and Vol. 9, S. Udenfriend and J. Meienhofer edit. 1987, which are incorporated herein by reference.

General solid-phase peptide synthesis was used for peptide synthesis. Such methods are described in "Solid-Phase Peptide Synthesis," Stewart and Young, Freeman and Co., San Francisco, 1969, which is incorporated herein by reference.

Peptides were synthesized on polystyrene resin crosslinked with 1% divinylbenzene. An acid sensitive linker was coupled to the solid support (Rink Linker) (Rink, Tetrahedron Lett. 28:3787 (1987); Sieber, Tetrahedron Lett. 28:2107 (1987)). Coupling was done by N,N'-diisopropylcarbodiimide (DIC) in the presence of an equivalent amount of HOBt. All couplings were done in DMF at room temperature for 120 minutes. Completion of coupling was monitored by the ninhydrin test. The deprotection of the 9-fluorenylmethyloxycarbonyl (Fmoc) group was accomplished with 50% piperidine in DMF for 10 minutes. The amount of Fmoc released was determined from the absorbance at 300 nm of the solution after deprotection, volume of washes, and weight of the resin used in the synthesis. A second (double) coupling was carried out in the case of incomplete coupling. The cycle of each coupling and methods can be summarized as follows:

| Step | Action | Reagent and Solvent |
|---|---|---|
| 1 | 1 g Peptide Resin | 10 mL DMF |
| 2 | 3 fold-excess amino acid derivative | |

-continued

| Step | Action | Reagent and Solvent |
|---|---|---|
| 3 | 3 equivalent | DIC |
| 4 | 3 equivalent | HOBt |
| 5 | Couple for 120 min | |
| 6 | Wash (3 × 8 mL) | DMF |
| 7 | Ninhydrin test | |
| 8 | Deprotection (10 min) | 8 mL 50% Piperidine/DMF |
| 9 | Wash (6 × 8 mL) | DMF |
| 10 | Repeat from step 2 | |

After completion of assembly of the peptide on the resin, the final Fmoc deprotection was accomplished as usual followed by normal wash cycles and determination of the amount of Fmoc group released by deprotection.

Peptide resin was suspended in reagent K (King et al., Int. J. Peptide Protein Res. 36:255–266 (1990) (5 mL/g peptide resin) for 180 minutes at room temperature. The cleavage mixture was filtered in anhydrous diethyl ether and the solid precipitate was isolated by centrifugation and dried in vacuum over solid pellets of KOH. The dried peptide was subjected to HPLC purification using a gradient of 0.1% TFA in water and acetonitrile. After collection of the peak containing the intended synthetic product, the peptide solution was lyophilized and the peptide subjected to an identification process which included electro/spray mass spectrometry, in addition to amino acid analysis to confirm that the correct compound had been synthesized.

For peptide purification, a sample of crude lyophilized peptide was dissolved in a mixture of 0.1% aqueous TFA containing 10 to 50% acetonitrile. The peptide solution was filtered through a syringe connected to a 0.45=E6m Gelman Nylon Acrodisc 13 (Gelman Sciences, Ann Arbor, Mich.) filter. A proper volume of filtered peptide solution was injected into a semiprep C18 column (Vydac Protein and Peptide C18, 218TP1010, The Separation Group, Hesperia, Calif. 92345). The flow rate of a gradient or isocratic mixture of 0.1% TFA buffer and acetonitrile (HPLC grade) as an eluent, was maintained using a Beckman Gold System HPLC. The elution of the peptide was monitored using UV detection (Beckman, System Gold, Programmable Detector Module 166) at a wavelength of 230 nm. After identifying the peak which corresponded to the compound under synthesis, using mass spectroscopy, the compound was collected, lyophilized and biologically tested.

6.2 LIBRARY SYNTHESIS

6.2.1 SUPPLIES, INSTRUMENTS AND PROCEDURES

Library syntheses were performed on TentaGel Resin S Amino-NH2 (Rapp Polymere, Tubingen, Germany) 12. Fmoc amino acids, with standard side chain protected groups, were obtained from Advanced ChemTech (Louisville, Ky.) Bachem (Torrance, Calif.) or Propeptide (Vert-le-Petit, France). Benzotriazolyl-oxy-trisdimethylamino-phosphonium hexafluorophosphate (BOP), N-hydroxybenzotriazole (HOBt), diisopropylethylamine (DIEA), piperidine and diisopropylcarbodiimide (DIC) were obtained from Advanced ChemTech. Commercial-grade solvents were used without further purification. 2-Bromo-3-chloro-indole phosphate (BCIP) was obtained from Ameresco (Solon, Ohio).

Sequencing by Edman degradation was performed on an ABI 4778 protein sequencer (Applied Biosystems, Foster City, Calif.) and Porton PI 3010 instrument (Porton Instruments, Tarzana, Calif.). Both analytical and preparative HPLC were carried out on a Waters 625 LC system with a Waters 490E Programmable Multiwavelength Detector using Vydac Peptide and Protein C18 analytical (0.46×250 mm, 5=E6 m, 1 mL/min) and preparative (10×250 mm, 10=E6 m, 3 mL/min) columns, respectively. UV/VIS absorption spectra were recorded on a Hewlett Packard HP 8452A Diode-Array spectrophotometer using a 1-cm quartz cuvette. Amino acid analyses were carried out on a D-500 system (Durrum Corp., Palo Alto, Calif.) system.

The randomization steps (based on the split synthesis methodology—(Lam et al., 1991, NATURE, 354:82) were performed in such a way that each bead was exposed only to a single activated amino acid at each coupling cycle and the coupling reaction was driven to completion. The mixture of protected amino acids with molar ratios adjusted according to the pilot experiment (see Table IIB infra), was used in steps in which a mixture of amino acids was coupled at the nonmotif positions. Alternatively, each nonmotif position was synthesized by two successive couplings. An equimolar mixture of amino acids in subequimolar quantity (1:0.8) was used in the first coupling and an excess of the same mixture was used in the second coupling. Standard solid phase peptide synthesis chemistry (Fmoc-chemistry) was used. For standard peptide libraries, polyethylene glycol grafted polystyrene bead or TentaGel-S were used.

Depending on the application, additional non-cleavable linkers such as Fmoc-aminocaproic acid, Fmoc-aminobutyric acid, and/or Fmoc-β-alanine, can first be added onto the resin prior to the amino acid randomization steps.

In the split synthesis randomization steps of the library synthesis, the resins were first divided into 19 aliquots contained in 19 polypropylene vials. Nineteen Fmoc protected natural amino acids (all but cysteine) were then added separately into each of the resin aliquots. Minimal amount of dimethylformamide (DMF) was used. The amino acids were added in 3 fold excess and coupling was initiated by adding 3 fold excess of BOP and HOBt. In some experiments DIC and HOBt were used instead. A trace amount of bromophenol blue was added into the reaction mixture. The vials were capped tightly and rocked gently for approximately 120 minutes at room temperature or until all beads turned from blue to colorless 14. Completion of the coupling was then confirmed by a ninhydrin test. For the aliquots in which coupling reactions were incomplete, the beads were allowed to settle and the supernatant gently removed. Fresh Fmoc-amino acid was then added to that vial followed by BOP and HOBt and the reaction allowed to proceed for another hour. In general, most randomization cycles required only one coupling and only on rare occasions was double coupling needed. The resins were then mixed in a siliconized cylindrical glass vessel fitted with a frit at the bottom. Dried N2 was bubbled through for mixing of the resin. After washing (8x) with DMF, 50% piperidine (in DMF) was added. After 10 minutes of bubbling with N2, the piperidine was removed and the resins washed 10 times with DMF. The amount of released fulvene-piperidine adduct was quantitated by UV spectrometry (302 nm). Stable level of substitution determined in this way throughout the library synthesis served as one of the quality control measures. The resins were then divided into aliquots again for another cycle of randomization or amino acid mixture coupling. After all steps were completed, the Fmoc group was removed with 20% piperidine (v/v) in DMF and the side chain protecting groups were removed with a mixture of trifluoroacetic acid-phenol-anisole-ethanedithiole (94:2:2:2; v/w/v/v) or reagent K (TFA-phenol-water-thiophenol-ethanedithiole, 82.5:5:5:5:2.5; v/w/v/w/v) (31). The resin was then washed thoroughly in DMF, neutralized with 10% DIEA (in DMF), thoroughly washed again, and stored in DMF at 4° C.

TABLE II

Ratios of Fmoc amino acids affording
their equimolar incorporation onto
TentaGel by DIC/HOBt procedure Molar Amino Acid Ratio

| A | Ala | 0.37 |
| D | Asp | 0.32 |
| E | Glu | 0.45 |
| F | Phe | 0.49 |
| G | Gly | 0.65 |
| H | His | 1.30 |
| I | Ile | 3.10 |
| K | Lys | 1.05 |
| L | Leu | 0.52 |
| M | Met | 0.42 |
| N | Asn | 0.69 |
| P | Pro | 0.70 |
| Q | Gln | 0.91 |
| R | Arg | 1.36 |
| S | Ser | 1.84 |
| T | Thr | 3.63 |
| V | Val | 1.50 |
| W | Trp | 0.95 |
| Y | Tyr | 0.41 |

Determination of amino acid ratios for equimolar incorporation

A mixture of Fmoc protected amino acids was coupled by the chosen method to the selected carrier. The ratio of amino acids used in this first approximation was based on the literature. Coupling was driven to completion, beads were deprotected and 10 of them were submitted to one cycle of Edman degradation. Ratios of incorporation were calculated and mixture concentration appropriately adjusted. The new ratios were applied for the same experiment again and the results of the second approximation were used for final adjustment of concentrations used for the library synthesis.

To verify the quality of the library, several randomly chosen beads were submitted for sequencing and the average amount of the peptide per bead was determined. This value was confirmed by quantitative amino acid analysis of a random sample from the library (1 mg). Amino acid analysis, as well as sequence analysis of pooled sample of beads (~50 beads) must confirm at the random distribution of all amino acids.

6.2.2 SYNTHESIS OF DEFINED PARAMETER HEXAMER. TRIPLET LIBRARY

Polyoxyethylene modified polystyrene (TentaGel S-NH2, Rapp Polymere Tubingen, Germany, 90 mm particle size, 0.29 mmol/g, 10 g) was swollen in DMF and Fmoc-Gly, Fmoc-β-Ala, Fmoc-Gly and Fmoc-β-Ala were coupled to it by diisopropylcarbodiimide/N-hydroxybenzotriazole (DIC/HOBt) procedure. Fmoc group was removed and resin was separated into two parts. One part ("1R1") was divided into 19 vessels and 19 Fmoc protected amino acids were coupled by DIC/HOBt procedure with bromophenol blue (BB) monitoring. The second part ("1M1") of the resin was acylated by the mixture defined in Table II using the same procedure. Part 1R1 was divided into two parts—"2R2" (⅓) and "2M2" (⅔), rather than ⅖ and ⅗ as specified above. Part 2R2 was divided into 19 aliquots and the coupling of Fmoc amino acids was performed. Part 2M2 was acylated by the mixture of amino acids. Part 1M1 was similarly divided into two parts—2M1 (⅓) and 2R1 (⅔), instead of the preferred mode of ⅖ and ⅗, and randomization was performed on part 2R1 and mixture of amino acids was coupled to part 2M1. No pooling was done until after the third coupling. The procedure of dividing into M and R parts continued. After the third step of the synthesis parts of the mixtures to follow identical paths were recombined. After all library aliquots were recombined, the library was deprotected and analyzed.

6.2.3 SYNTHESIS OF A TRIPLET, VARIABLE INTERVAL TRIMER LIBRARY

This library was synthesized according to FIG. 2. After the assembly of the linker, ¼ of the resin was removed from the reactor and a mixture of amino acids (Table II) was coupled. Another part (⅓) of the resin was removed, the rest was deprotected and the mixture was coupled. After complete coupling the half of the resin was removed and remaining resin deprotected (Fmoc) and the mixture coupled again. All resin portions were recombined and the Fmoc group was removed. The resin was divided into 19 aliquots and split synthesis was performed. This procedure was repeated until the full length of the library was achieved. Deprotection of the library and analytical control was performed as described above.

6.2.4 HEXAPEPTIDE MOTIF LIBRARY OF DIASTEREOISOMERIC PEPTIDES WITH THREE MOTIF POSITIONS

Polyoxyethylene modified polystyrene (TentaGel S-NH2, Rapp Polymere Tubingen, Germany, 90 mm particle size, 0.29 mmol/g, 50 g) was swollen in DMF and Fmoc-Gly, Fmoc-b-Ala, Fmoc-Gly and Fmoc-b-Ala were coupled to it by diisopropylcarbodiimide/N-hydroxybenzotriazole (DIC/HOBt) procedure. Fmoc group was removed and resin was separated into three parts. One part (½—1R1) was divided into 78 vessels. Into some of these vessels (see Table III D, entries marked "pre") a defined coding amino acid was added in 0.05 molar ratio together with carbodiimide and HOBt, and coupling was performed for 1 h. Only after this period the excess of randomized amino acid together with the activator was added to all 78 vessels. In the cases marked mix, the randomized amino acid was mixed with 0.05 equivalents of coding amino acid. The second part of the resin (¼) was acylated by the mixture of L- amino acids and the third part (¼) was acylated by the mixture of D-amino acids and norleucine (ratio given in Table III). The synthesis proceeded as in the case of section 6.2.3, except that at the couplings of nonmotif positions, the fractions were divided into two parts and coupled with mixtures of L and D amino acids separately. After all library aliquots were recombined, the library was deprotected, as above, and analyzed.

TABLE III

Set of building blocks (and their coding) used in the diastereoisomeric library of libraries

| Amino acid | Coded by | added when | M.w. | Abre. | R.t.c |
|---|---|---|---|---|---|
| Fmoc-L-Alanine | | | 311.3 | A | 14.07 |
| Fmoc-D-Alanine | G | mix | 311.3 | a | 14.07 |
| Fmoc-Aminoisobutyric acid | A | pre | 325.3 | Aib | 18.6 |
| Fmoc-3-(3-pyridyl)-L-Alanine | A | mix | 389.6 | 3-Pal | 14.53 |
| Fmoc-3-(3-pyridyl)-D-Alanine | f | mix | 389.6 | 3-pal | 14.53 |
| Fmoc-beta-thienyl-L-Alanine | | | 393.4 | Tha | 25.9 |
| Fmoc-beta-thienyl-D-Alanine | G | mix | 393.4 | tha | 25.9 |
| Fmoc-cyclohexyl-L-Alanine | | | 393.5 | Cha | 38.88 |
| Fmoc-cyclohexyl-D-Alanine | G | mix | 393.5 | cha | 38.88 |
| Fmoc-aminobutyric acid | | | 325.3 | Abu | 18.77 |
| Fmoc-N-b-Boc-L-Diaminopropionic | Dab | mix | 426.5 | Dap | 26.28 |
| Fmoc-N-g-Boc-L-diaminobutyric | Dap | mix | 441.5 | Dab | 26.9 |
| Fmoc-L-Arginine(Pmc) | | | 662.8 | R | 20.62 |
| Fmoc-D-Arginine(Pmc) | G | pre | 662.8 | r | 20.62 |
| Fmoc-L-Asparagine(Trt) | | | 596.7 | N | 6.77 |
| Fmoc-D-Asparagine(Trt) | G | pre | 596.7 | n | 6.77 |
| Fmoc-L-Aspartate(OBut) | | | 411.5 | D | 6.33 |
| Fmoc-D-Aspartate(OBut) | G | mix | 411.5 | d | 6.33 |
| Fmoc-L-Aspartate(OAllyl) | | | 395.4 | | 24.02 |
| Fmoc-N-methyl-L-Aspartate(OBzl) | | | 459.5 | | 36.03 |
| Fmoc-L-Cysteine(Acm) | | | 414.5 | C(Acm) | 12.75 |
| Fmoc-L-Glutamate(OBut) | | | 425.5 | E | 10.87 |
| Fmoc-D-Glutamate(OBut) | G | mix | 425.5 | e | 10.87 |
| Fmoc-L-Glutamate(OAllyl) | | | 409.4 | | 26.85 |
| Fmoc-L-Glutamine(Trt) | | | 611.8 | N | 8.42 |
| Fmoc-D-Glutamine | G | pre | 368.4 | n | 8.42 |
| Fmoc-Glycine | | | 297.3 | G | 9.62 |
| Fmoc-MeGly(Sarcosine) | | | 311.3 | Sar | 13.82 |
| Fmoc-L-Histidine(Trt) | | | 619.7 | H | 14.75 |
| Fmoc-D-Histidine(Trt) | G | pre | 619.7 | h | 14.75 |
| Fmoc-L-Isoleucine | Nle | pre | 353.4 | I | 28.68 |
| Fmoc-D-Isoleucine | G,Nle | pre | 353.4 | i | 28.68 |
| Fmoc-allo-Isoleucine | V | mix | 354.3 | aIle | 28.6 |
| Fmoc-N-methyl-L-Isoleucine | | | 367.4 | MeIle | 35.3 |
| Fmoc-L-Leucine | | | 353.4 | L | 29.55 |
| Fmoc-D-Leucine | G | mix | 353.4 | l | 29.55 |
| Fmoc-N-methyl-L-Leucine | A | pre | 367.4 | MeLeu | 35.15 |
| Fmoc-L-Lysine(Boc) | | | 468.6 | K | 29.12 |
| Fmoc-D-Lysine(Boc) | G | pre | 468.6 | k | 29.12 |
| Fmoc-L-Lysine(Alloc) | | | 452.5 | | 26.45 |
| Fmoc-L-Methionine | | | 371.5 | M | 23.23 |
| Fmoc-D-Methionine | G | mix | 371.5 | m | 23.23 |
| Fmoc-L-Norleucine | A | mix | 353.4 | Nle | 30.11 |
| Fmoc-L-Ornithine(Boc) | | | 454.5 | Orn | 27.53 |
| Fmoc-D-Ornithine(Boc) | G | pre | 454.5 | orn | 27.53 |
| Fmoc-L-Phenylalanine | | | 387.4 | F | 28 |
| Fmoc-D-Phenylalanine | G | mix | 387.4 | f | 28 |
| Fmoc-p-amino(Boc)-L-Phenylalanine | | | 502.6 | Aph | 30.26 |
| Fmoc-p-nitro-L-Phenylalanine | A | mix | 432.4 | Nph | 28.19 |
| Fmoc-p-fluoro-L-Phenylalanine | F | mix | 405.4 | Phe(F) | 29.26 |
| Fmoc-N-methyl-L-Phenylalanine | | | 401.4 | MePhe | 32.77 |
| Fmoc-L-Proline | | | 337.4 | P | 21.93 |
| Fmoc-D-Proline | G | mix | 337.4 | p | 21.93 |
| Fmoc-L-Serine(But) | | | 383.4 | S | 8.03 |
| Fmoc-D-Serine(But) | G | pre | 383.4 | s | 8.03 |
| Fmoc-L-Threonine(But) | | | 397.5 | T | 9.18 |
| Fmoc-D-Threonine(But) | G | pre | 397.5 | t | 9.18 |
| Fmoc-L-Tryptophan | | | 426.5 | W | 27.13 |
| Fmoc-D-Tryptophan | G | pre | 426.5 | w | 27.13 |
| Fmoc-L-Tyrosine(But) | | | 459.5 | Y | 18.5 |
| Fmoc-D-Tyrosine(But) | G | mix | 459.5 | y | 18.5 |
| Fmoc-3-nitro-L-Tyrosine | | | 448.4 | Ty(NO2) | 26.18 |
| Fmoc-L-Valine | | | 339.4 | V | 23.62 |
| Fmoc-D-Valine | G | pre | 339.4 | v | 23.62 |
| Fmoc-L-Norvaline | | | 339.4 | Nva | 24.76 |
| Fmoc-L-tert-leucine | | | 353.5 | Tle | 28.56 |

TABLE III-continued

Set of building blocks (and their coding)
used in the diastereoisomeric library of libraries

| Amino acid | Coded by | added when | M.w. | Abre. | R.t.c |
|---|---|---|---|---|---|
| Fmoc-D-tert-leucine | G | pre | 353.5 | tle | 28.56 |
| Fmoc-cyclohexyl-Glycine | | | 379.5 | Chg | 34.1 |
| Fmoc-p-hydroxy-L-Phenylglycine | A | pre | 390.4 | Hgl | 20.85 |
| Fmoc-(1-napthyl)-L-Alanine | | | 437.5 | 1-Nal | 35.75 |
| Fmoc-(2-napthyl)-L-Alanine | | | 437.5 | 2-Nal | 35.05 |
| Fmoc-L-Tic | | | 399.4 | Tic | 36.4 |
| Fmoc-D-Tic | G | pre | 399.4 | tic | 36.4 |
| Fmoc-L-7-OH-Tic | Tic | mix | 415.4 | Tic(OH) | 27.23 |
| Fmoc-S-benzyl-D-Penicillamine | | | 461.6 | pen | 40.2 |
| Fmoc-L-Citrulline | A | pre | 397.6 | Cit | 9.06 |
| Fmoc-D-Citrulline | G, A | pre | 397.6 | cit | 9.06 |
| Fmoc-L-3-(4-thiazolyl)alanine | | | 395.5 | Ala(Th) | 16.32 |

R.t. = retention time

6.3 RESULTS OBTAINED BY USE OF THE INVENTION

We have prepared both a hexamer, triplet defined parameter library and a triplet, random trimer interval library by randomized synthesis with 19 natural amino acids (Cys omitted). The library was screened in three model systems — binding to anti-β-endorphin monoclonal antibody, to streptavidin, and to thrombin. Colorized beads were selected, destained and incubated with the same concentration of the acceptor in the presence of the known specific competitor (YGGFL, LHPQF, fPRPG) to prove the specificity of the binding. Beads which did not stain in this second experiment were regarded as specific binders and were washed and stained again in the absence of the competitor. Numbers of stained, is competed and restained beads are given in Table IV is a comparison of the numbers obtained in screening conventional one bead one structure library.

TABLE IV

Comparison of the screening of model
targets with classical pentapeptide
library and with library of libraries

| Target | Library | Sample Size | Stained | Competed | Restained |
|---|---|---|---|---|---|
| Anti-β-endo | 5 (19)* | 10⁶ | >1000 | 160/-300 | 35/35 |
| Anti-β-endo | 6 (3F(19))** | 2 × 10⁵ | 16 | 16/16 | 16/16 |
| Avidin | 5 (19) | 10⁶ | >1000 | 43/100 | 43/43 |
| Avidin | 6 (3F(19)) | 10⁶ | 65 | 62/65 | 62/62 |
| Thromb | 5 (19D) | 10⁶ | 380 | 126/380 | 126/126 |
| Thromb | 6 (3F(19) | 3 × 10⁵ | 30 | 28/30 | 13/28 |

*A complete pantamer library having one species per support, 19 amino acids used in each split synthesis.
**A defined parameter triplet, hexamer library, 19 amino acids used in each coupling.

The ligands selected from the library of libraries were much more likely to be competitively inhibited by the specific peptides. The obvious conclusion to be drawn from these data is that there is a significantly higher probability of obtaining specific ligands from the motif libraries.

The identified beads are sequenced by Edman degradation. Positions containing defined amino acids are clearly marked by a single amino acid signal equal to the amount of total content of peptide on the bead (~50–150 pmoles). Positions containing a mixture of amino acids yield all amino acids used for the randomization in 20 times lower amount (2–7 pmoles).

6.3.1 A VARIABLE INTERVAL LIBRARY

Results of the screening of variable length library with anti-β-endorphin and streptavidin are given in Table VA.

TABLE V

Results of the screening of variable
interval motif library (tri to
pentadecapeptides)

A. Anti-β-endorphin
X G A F X X X
X G A F X X X
X G A F X X X
X G G F
B. Streptavidin
X X W X X X H P X X X
X X N X P X F X X X
X W X X X P Q X X X Anti-β-endorphin binding was observed on beads containing XGAF or XGGF sequence. Surprisingly, an N-terminal tyrosine was not observed. The reason for this finding might be statistical — the tested sample of the library was not large enough to completely represent all motifs.

Sequences identified as the ligands for streptavidin are given in Table VB. The motifs WXXXPQ and WXXXHP were identified and were not previously known to be streptavidin binders. The known motif HPQ was not observed, probably due to small sample tested ("a complete" variable interval library would require 1,755,904 beads).

6.3.2 A DEFINED PARAMETER LIBRARY

Results obtained with the defined prameter motif libraries are given in the Tables VI–VIII. It is obvious that antibody screening (Table IV) confirmed earlier findings Lam et al., 1991, NATURE 354:82; Lam et al., 1993 BIOORG MED. CHEM. LETL. 31:419 of YG(G/A)(F/W) as the very strong binding motif for the anti-β-endorphin antibody.

TABLE VI

Sequences binding to anti-β-endorphin
antibodies (sequences are listed in the
order of staining intensity)

| 1st experiment | 2nd experiment |
|---|---|
| Y G x F x x highest | Y G A x x x highest |
| Y ? x F x x | Y x G F x x |
| Y x G F x x | Y G x W x x |
| x G A F x x | Y G x F x x |
| Y G x F x x | Y G x F x x |
| Y G A F x x | x G G F x x |
| Y G x F x x | Y G G x x x |
| Y x A F x x | x G G F x x |
| Y ? A F x x | Y x G F x x lowest |
| x ? G F x x | |
| x G A F x x | |
| x G A F x x | |
| x G A F x ? lowest | |

Even the hits not containing Tyr very clearly indicated the importance of placement G(G/A)F motif separated by one amino acid from amino terminus. In general, sequences without defined N-terminus were classified as weaker binders according to the staining intensity. Streptavidin binding (Table VII) revealed known motif HP(Q/M).

TABLE VII

Sequences found positive and specific for binding to streptavidin (sequences are listed in the order of staining intensity)
? = position undeterminable.

| 1st experiment | 2nd experiment |
|---|---|
| x x x H P Q highest | x x x H P M highest |
| x x x H P Q | x x x H P Q |
| x x x H P Q | x ? x ? H P |
| x x x H P Q | x x x H P - |
| x x x H P Q | x x x ? P Q |
| x x H P Q x | H P Q x x x |
| W x x x P ? | x x H P M x |
| x x x H P M | x R x H P x |
| x W x H P x | w x x x P Q |
| W ? x H P x | x x W H P x |
| W x x H P x | x H P Q x x |
| H P Q x x x | x x P Q F x |
| H P x F x x lowest | x H x x F ? |
| | F x x ? P Q |
| | w x x x P M |

However, alternative motifs (W/F)_ _ _ P(Q/M) and HP_F were identified, as well as a motif in which tryptophan is either directly attached or separated by up to three amino acid residues from histidyl-proline sequence. The longer motifs identified in this library could not be observed in pentapeptide libraries and they were apparently overlooked in the longer libraries.

TABLE VIII

Sequences identified as positive and specific in the thrombin screening (sequences are listed in the order of staining intensity)

I R x W x x highest
I x F x Y x
I F x W x x
I x F W x x
I x F W x x
I R W x x x
L R x W x x
I R W x x x
L R Y x x x
L R Y x x x
L R Y x x x
I x F R x x
I R Y x x x lowest Binding to thrombin clearly identified hits (Table VIII) which we have not found in the classical peptide libraries. Isoleucine was clearly preferred in position 1 and arginine in position 2. Aromatic amino acid (phenylalanine or tyrosine) was found in position 3 and tryptophan in position 4. The composite peptide IRYWA was synthesized and tested for binding in solution, and it was found stronger inhibitor than the best peptide identified in peptide libraries (fFRPG).

Identified sequences were resynthesized both bound to the resin beads and in the free form. Bead bound peptide mixtures were stained under the same conditions as in the library screening and the staining was confirmed. Competition experiment (staining in the presence of the competitor) verified the specificity of the binding. Affinities of the mixtures towards the specific targets were determined by the solution assay, and the general correlation of the staining intensity on the bead surface with the binding constant was proven. The idea of replacing the amino acid mixture in the nonrandomized position by some single, indifferent amino acid was tested. We synthesized analogs of the found sequences with alanine in positions originally occupied by mixture.

Binding to these analogs was tested both on the solid surface and in solution. Alanine substitution in position 1 and 4 of anti-β-endorphin ligand and in all positions of thrombin ligand dramatically decreased binding. We can conclude that in these cases that more than three residues are necessary for the binding. Thus, only fraction of the peptide mixture containing the proper motif accounts for all the observable binding. These results will illustrate the superiority of the use of mixtures of large numbers of species of amino acids rather than one or two supposed indifferent amino acids at the nonmotif positions.

6.3.3 A DEFINED PARAMETER LIBRARY MADE USING 78 SPECIES OF MONOMERS

The success of motif libraries in the model systems prompted us to synthesize a more complex motif library employing 78 natural and unnatural amino acids of both D and L configuration in the three motif positions in a hexapeptide. Nonmotif positions were occupied by a mixture of either 18 L amino acids or 18 D amino acids. In positions in which a mixture of amino acids was to be coupled the resin was divided into two parts and one of two different mixtures were coupled to either of the D-mixture or the L-mixture. To be able to determine which mixture (D or L) was used in the given position, trace quantities of norleucine was added to the mixture of D-amino acids. The same strategy was used in the cases in which two amino acids used in a split synthesis had the same or very close retention time in the analysis. D amino acids were coded by the addition of glycine (5%). Sixteen amino acids had to be coded in this way as described in Table III. In the cases where the reactivity of coding and coded amino acid were comparable (e.g. Ile and Val), the mixture (1:20) was created and used for the coupling. In the cases of different reactivities (e.g. Gly and Ile), the couplings were performed in two steps. In the first step 0.05 equivalents of coding amino acid was pre-coupled for 1 h and only after this period three molar excess of coded amino acid was coupled in the usual way. A typical example of sequencing and decoding of one bead from this library is as follows. In the first cycle the mixture of all amino acids is observed, together with the signal of norleucine, which means that this mixture was composed from D amino acids. In the second cycle leucine was identified, in the third cycle 1-naphthylalanine was detected, in the fourth cycle mixture of L-amino acids was found (no Nle signal). Lysine signal in the fifth cycle was accompanied by glycine and therefore D configuration of lysine was deduced. Mixture of D-amino acids in the sixth cycle was found based on the Nle signal.

Due to the number of building blocks and stereochemical diversity this library could not be screened completely. A complete library would contain $7.59 \times 10^7$ motifs. However, screening of a sample provided important information about the motif required for the binding. An example of the results from the screening of this library with streptavidin is given in the Table IX. The known ligand HPQ was not found, but clearly its analogs were identified. The probability of finding HPQ sequence was 1:5,000,000 but only 1 million of beads were screened.

TABLE IX

Sequences found positive and specific for binding to streptavidin in the Library of Libraries constructed from 78 building blocks and mixtures of D and L amino acids (sequences are listed in the order of staining intensity). Lower case x denotes mixture of D amino acids, upper case X denotes mixture of L amino acids.

His - Tic -x-Lys(Alloc)-X - X
X - His-(Me)Phe -X-Lys-X
X - X - His-(Me)Phe - Lys(Alloc) - X
X - X - x - Tic - His-(Me)Phe
x - x - X - Tyr(3-NO2)-Pro - Tha The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

We claim:

1. A library consisting of a multiplicity of sets, each said set comprising a multiplicity of species of test ligands, in which:
   a) each species of test ligand of the library comprises a linker and a multiplicity of monomers, wherein:
      i) said monomers are selected from a multiplicity of species of monomers; and
      ii) said linker connects the monomers of a species of test ligand to a solid phase support particle or to an identifiable location of a solid support;
   b) each monomer is disposed in one of a predetermined number of motif positions or in one of a predetermined or variable number of nonmotif positions, wherein:
      i) the motif and non-motif positions have an ordered sequence; and
      ii) there are a plurality of motif positions in each set of the library;
   c) all species of test ligands of a particular set have:
      i) a constant number of nonmotif positions and an identical, single ordered sequence of motif and non-motif positions;
      ii) an identical, single species of monomer, selected from a plurality of species of monomer, at each of the predetermined number of motif positions; and
      iii) one of a plurality of species of monomers at each of the constant number of nonmotif positions;
   d) all species attached to a particular solid phase particle or to a particular identifiable location of a solid support are encompassed by a single set; and
   e) the library is a complete collection of sets in which all possible particular ordered
      (i) sequences of the motif positions and nonmotif positions or
      (ii) sequences of motif positions and intervals of non-motif positions are represented.

2. The library of claim 1 in which the number of nonmotif positions is predetermined.

3. The library of claim 1 in which the number of nonmotif positions is variable and there are a variable number, said number being between 0 and N, of nonmotif positions between every motif position.

4. The library of claim 3 in which N is 1, 2, or 3.

5. The library of claim 1 in which every species of test ligand is attached to a solid phase support particle.

6. The library of claim 1 in which every species of test ligand is disposed in a vessel and wherein no said vessel contains a plurality of sets of test ligands.

7. The library of claim 6 in which every species of test ligand is attached to a solid phase support.

8. The library of claim 1 in which every species of test ligand is attached to an identifiable portion of a solid phase support and wherein no said identifiable portion comprises a plurality of sets of test ligands.

9. The library of claim 1 in which the selection of a species of monomer at a particular motif position of a test ligand is independent of the selection of the species of monomers at all other motif positions of said test ligand.

10. The library of claim 1 wherein, at each nonmotif position, the monomer is selected from a multiplicity of species of monomers.

11. The library of claim 10 wherein, at each nonmotif position, each species of monomers is selected from an identical multiplicity of species of monomers.

12. The library of claim 1 in which the solid phase support is selected from the group consisting of silica gels, resins, plastic films, derivatized plastic films, glass beads, cotton, plastic beads, plastic sheets, glass sheets and polysaccharides.

13. The library of claim 12 in which the solid phase support is a resin selected from the group consisting of polystyrene, polyamide, polydimethylacrylamide, polyamide, and polystyrene resin grafted with polyethylene glycol.

14. The library of claim 1 in which the monomers of the test ligand are linked by chemical bonds selected from the group consisting of amide, ester, urea, urethane, carbonate, amine, alkane, alkene, sulfide, and disulfide.

15. The library of claim 1 in which the test ligand consists of a linker and a polymer selected from the group consisting of polyamide, polyester, polyurea, polyurethane, polycarbonate, polyamine, polyalkane, polyalkene, polyalcohol, polysulfide and polydisulfide.

16. The library of claim 1 in which the linker comprises a molecular scaffold.

17. The library of claim 16 in which the molecular scaffold is selected from the group consisting of a steroid structure, a sugar, a heterocyclic structure, and a polyaromatic compound.

18. The library of claim 1 in which the predetermined number of motif positions is less than 10.

19. The library of claim 18 in which the predetermined number of motif positions is 3.

20. The library of claim 18 in which the predetermined number of motif positions is 4.

21. The library of claim 1 in which the number of nonmotif positions is less than 20.

22. The library of claim 21 in which the number of nonmotif positions is 3 or greater.

23. The library of claim 21 in which the number of nonmotif positions is 4 or greater.

24. The library of claim 21 in which the number of nonmotif positions is 6 or greater.

25. The library of claim 5 in which a species of coding molecule is attached to each solid phase support, whereby the species of monomer at each motif position of the species test ligands attached to said support is determinable from the structure of the coding molecule.

26. The library of claim 25 in which the coding molecule and the test ligand are topologically separable.

27. The library of claim 6 which further comprises a species of coding molecule corresponding to each vessel, whereby the species of monomer at each motif position of test ligands contained in said vessel are determinable from the structure of the coding molecule.

* * * * *